(12) United States Patent
Collmer et al.

(10) Patent No.: US 7,109,397 B2
(45) Date of Patent: Sep. 19, 2006

(54) PSEUDOMONAS SYRINGAE HARPINS, HOPPTOP AND HOPPMAH$_{PTO}$, AND THEIR USES

(75) Inventors: Alan Collmer, Ithaca, NY (US); Adela Ramos, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 102 days.

(21) Appl. No.: 10/355,956

(22) Filed: Jan. 30, 2003

(65) Prior Publication Data

US 2004/0006789 A1      Jan. 8, 2004

Related U.S. Application Data

(60) Provisional application No. 60/380,185, filed on May 10, 2002, provisional application No. 60/356,408, filed on Feb. 12, 2002.

(51) Int. Cl.
- *A01H 5/00* (2006.01)
- *A01H 5/10* (2006.01)
- *C12N 15/82* (2006.01)
- *C12N 15/31* (2006.01)

(52) U.S. Cl. ............... 800/301; 800/279; 536/23.7; 424/93.2

(58) Field of Classification Search ............... 536/23.4; 435/320.1; 800/279
See application file for complete search history.

(56) References Cited

U.S. PATENT DOCUMENTS

| | | |
|---|---|---|
| 6,172,184 B1 | 1/2001 | Collmer et al. |
| 6,228,644 B1 | 5/2001 | Bogdanove et al. |
| 6,262,018 B1 | 7/2001 | Kim et al. |
| 6,277,814 B1 | 8/2001 | Qiu et al. |
| 6,342,654 B1 | 1/2002 | Li et al. |

FOREIGN PATENT DOCUMENTS

WO      WO 99/07207     *  2/1999

OTHER PUBLICATIONS

Lazar et al., Mol. Cell. Biol. 8:1247-1252, 1988.*
Hill et al., Biochem. Biophys. Res. Comm. 244:573-577, 1998.*
Guo et al., Protein Tolerance To Random Amino Acid Change. Proceedings of the National Academy of Sciences of The United States of America, 101:9205-9210, 2004.*
Fouts et al., "Genomewide Identification of *Pseudomonas syringae* pv. *tomato* DC3000 Promoters Controlled by the HrpL Alternative Sigma Factor," *Proc. Natl. Acad. Sci. USA* 99(4):2275-2280 (2002), including supplemental notes located online at http://www.pnas.org.
Petnicki-Ocwieja et al., "Genomewide Identification of Proteins Secreted by the Hrp Type III Protein Secretion System of *Pseudomonas syringae* pv. *tomato* DC3000," *Proc. Natl. Acad. Sci. USA* 99(11):7652-7657 (2002), including supplemental notes located online at http://www.pnas.org.
Guttman et al., "A Functional Screen for the Type III (Hrp) Secretome of the Plant Pathogen *Pseudomonas syringae*," *Science* 295(5560):1722-1726 (2002) (including Supplemental Notes, located online at http://pseudomonas-syringae.org/pdf/Guttman,2002-suppl.pdf).
Collmer et al., "*Pseudomonas syringae* Hrp Type III Secretion System and Effector Proteins," *PNAS* 97(16):8770-8777 (2000).
Alfano et al., "The *Pseudomonas syringae* Hrp Pathogenicity Island has a Tripartite Mosaic Structure Composed of a Cluster of Type III Secretion Genes Bounded by Exchangeable Effector and Conserved Effector Loci That Contribute to Parasitic Fitness and Pathogenicity in Plants," *PNAS* 97(9):4856-4861 (2000).
Fouts et al., "Genomewide Identification of *Pseudomonas syringae* pv. Tomato DC3000 Promoters Controlled by the HrpL Alternative Sigma Factor," *PNAS* 99(4):2275-2280 (2002), with supplemental material available online at www.pnas.org.
Petnicki-Ocwieja et al., "Genomewide Identification of Proteins Secreted by the Hrp Type III Protein Secretion System of *Pseudomonas syringae* pv. Tomato DC3000," *PNAS* 99(11):7652-7657 (2002), with supplemental material available online at www.pnas.org.
Zwiesler-Vollick et al., "Identification of Novel *hrp*-regulated Genes through Functional Genomic Analysis of the *Pseudomonas syringae* pv. Tomato DC3000 Genome," *Molecular Microbiology* 45(5):1207-1218 (2002).

* cited by examiner

*Primary Examiner*—Anne Kubelik
(74) *Attorney, Agent, or Firm*—Nixon Peabody LLP

(57) ABSTRACT

The present invention relates to isolated DNA molecules that encode proteins or polypeptides which elicit a hypersensitive response in plants. One aspect of the present invention involves an isolated DNA molecule that encodes the HopPtoP protein of *Pseudomonas syringae* pv. tomato DC3000. The isolated DNA molecules can be used to impart disease resistance, stress resistance, and enhanced growth to plants or plants grown from treated seeds, to control insects on plants or plants grown from treated plant seeds, to impart post-harvest disease or desiccation resistance in fruits or vegetables, to impart enhanced longevity of fruit or vegetable ripeness, to impart desiccation resistance to cuttings of ornamental plants, and/or promote early flowering of ornamental plants, either by topical application of the proteins or polypeptides or transgenic expression in recombinant plants or plant seeds. Expression vectors, host cells, and transgenic plants which include the DNA molecules of the present invention are disclosed.

40 Claims, 4 Drawing Sheets

HopPmaH_Pto · Negative Control · HrpZ · HopPtoP

SEQUENCE LISTING

```
<160> NUMBER OF SEQ ID NOS: 8

<210> SEQ ID NO 1
<211> LENGTH: 975
<212> TYPE: DNA
<213> ORGANISM: Pseudomonas syringae

<400> SEQUENCE: 1
atgaccatgg gtgtttcacc tattcgtaac tcaaactccc tgccgatcga ttttcgtcg      60 ttgagcgcaa agagtggcgg gcataacggg ctgggcagcg gagacaattc gactatcgac    120
ccgagtacgt tgttgttcgg caatcaaggg cagacgcagg tcaatttcgc tccgcccaac    180
agcacggact cctcaaccag cggtgtgaac gctgcgtcag gcaatacggc gtccggcctg    240
```

-continued

```
gtcgagcaaa tcatgagcct gctgaaacaa ttgatgcaga tgctgatgca aaacaacaat      300
gcttccggta accctcagac tgattcgtca acgccaggcg tcggcagtgg caacagcgtc      360
gggagcggcg gtactggaag cagtctcgca ggcagtgacg gtggcgacga aacgtccggt      420
gtcggtaacg gcggtttagg cgacgcgggc agcacgccaa caacgagcgc ggccgatggt      480
gtgccctcgg atacttcact cacgggtagc ggtgggctgc atttgcctca acagcttgag      540
cagtatcgag gcgacattat ggacgccgcc aaagccaccg gcgtgccgcc cagcgtgatc      600
gccgggcaga tatgggctga gtcgcgcggt cagttgaatg cggccaccac caatgtcaac      660
ggcaaggccg atgcgggcct gatgcaggtc aacgcagaca cgttcaagtc attgcagcag      720
caaaacccgg ggttgctggg caacgacgtc aacgattcgc acaccaacat catggcgggc      780
gcgctctacc tgcgagacca gaacaaggag ttcggcgaca tgggggcagc acttcgcgca      840
tacaactccg ggcccgacaa ggtcaataaa gccgacctca gcgacacggg aggcgtgggc      900
ggcagcagct acccggcgga cgtactgaac ttcgcgaaaa tcatcgagag tgggcagggc      960
aatttacccg cttga                                                       975
```

<210> SEQ ID NO 2
<211> LENGTH: 324
<212> TYPE: PRT
<213> ORGANISM: Pseudomonas syringae

<400> SEQUENCE: 2

```
Met Thr Met Gly Val Ser Pro Ile Arg Asn Ser Asn Ser Leu Pro Ile
  1               5                  10                  15

Asp Phe Ser Ser Leu Ser Ala Lys Ser Gly Gly His Asn Gly Leu Gly
             20                  25                  30

Ser Gly Asp Asn Ser Thr Ile Asp Pro Ser Thr Leu Leu Phe Gly Asn
         35                  40                  45

Gln Gly Gln Thr Gln Val Asn Phe Ala Pro Pro Asn Ser Thr Asp Ser
     50                  55                  60

Ser Thr Ser Gly Val Asn Ala Ala Ser Gly Asn Thr Ala Ser Gly Leu
 65                  70                  75                  80

Val Glu Gln Ile Met Ser Leu Leu Lys Gln Leu Met Gln Met Leu Met
                 85                  90                  95

Gln Asn Asn Asn Ala Ser Gly Asn Pro Gln Thr Asp Ser Ser Thr Pro
            100                 105                 110

Gly Val Gly Ser Gly Asn Ser Val Gly Ser Gly Thr Gly Ser Ser
        115                 120                 125

Leu Ala Gly Ser Asp Gly Gly Asp Glu Thr Ser Gly Val Gly Asn Gly
    130                 135                 140

Gly Leu Gly Asp Ala Gly Ser Thr Pro Thr Ser Ala Ala Asp Gly
145                 150                 155                 160

Val Pro Ser Asp Thr Ser Leu Thr Gly Ser Gly Leu His Leu Pro
                165                 170                 175

Gln Gln Leu Glu Gln Tyr Arg Gly Asp Ile Met Asp Ala Ala Lys Ala
            180                 185                 190

Thr Gly Val Pro Pro Ser Val Ile Ala Gly Gln Ile Trp Ala Glu Ser
        195                 200                 205

Arg Gly Gln Leu Asn Ala Ala Thr Thr Asn Val Asn Gly Lys Ala Asp
    210                 215                 220

Ala Gly Leu Met Gln Val Asn Ala Asp Thr Phe Lys Ser Leu Gln Gln
225                 230                 235                 240
```

```
Gln Asn Pro Gly Leu Leu Gly Asn Asp Val Asn Asp Ser His Thr Asn
                245                 250                 255

Ile Met Ala Gly Ala Leu Tyr Leu Arg Asp Gln Asn Lys Glu Phe Gly
            260                 265                 270

Asp Met Gly Ala Ala Leu Arg Ala Tyr Asn Ser Gly Pro Asp Lys Val
        275                 280                 285

Asn Lys Ala Asp Leu Ser Asp Thr Gly Val Gly Gly Ser Ser Tyr
    290                 295                 300

Pro Ala Asp Val Leu Asn Phe Ala Lys Ile Ile Glu Ser Gly Gln Gly
305                 310                 315                 320

Asn Leu Pro Ala

<210> SEQ ID NO 3
<211> LENGTH: 1668
<212> TYPE: DNA
<213> ORGANISM: Pseudomonas syringae

<400> SEQUENCE: 3
atgaatacga tcaacagaaa catctacccc gtctccggga tttctgcgca ggatgcccct       60
gtacaaactg atcagctcca gccgcaaggc cagggcatca ggccgggca  caatagcaac     120
ctgatcgact tcggactgat acagcaggcc aatggtccgc actcatcgct gaacacatcg      180
agctccagaa ttcagccgac tgacaccagc acatcctcaa acaggctggg gggtaatggc      240
gatcagttac tgaacaaact cgtggaagcg atccgtaata tcctcaacaa cctgctctct      300
ctgctggaag gcaatcaaca ccagggctct tcgcctgcac agacccagcg tgaacagacg      360
ccgacgtcca ctcaatcgca cgcttcgcct tcctcgtcgt cttcatcttc gccgtcgaca      420
tcctcccagt cttcacccct cagtgccttca acgcctcagg gcaacgcaga aaaaccgttt     480
gtggtgcaga gcgatcatcc ggcggaaaaa ccggtatcgc tgcagagaac ctcagagcca      540
acgtctgtga cgccgccaca aacaccaccg caggctgtcg agcgaaacag cattaccccg      600
gacaaggcac cggccaaacc cgaagcggta agccggcag  tggtcaacga cccggtgctg     660
ccgaaaacct cgatccctgc cgccgccaag cctgacagca cggtgaccgc cgcaaaacac      720
gcgacgcccg ctgcccgtgg ccagggcgct gacatgtccg gcatgatcgg ttttgccaag      780
gaagccaata ccaccggggg caacaacggc gaagtggtca ccgtgaacac ggttgccgac      840
ctcaagaagt acatggagga cgacaaagcc cgcaccgtca agctgggggc caacctgtct      900
gccgacagta aagtgtcgat aaatttcggg gccaacaaaa ccctgctggg caccgataaa      960
ggcaacaccc tgcacaacat ctatctggcc agcggcaaga ccgccagcaa cgacattttc     1020
cagaatctga acttcaacca cgacgcccgt taccgtgaaa acggcgacat gcagatgttc     1080
atcagcagcg gtcagaaata ctggatcgac cacatcaccg ctaccggaac caaggatcag     1140
aaccccaaag gtctggataa actgctctac gtgggcggca aggcagataa cgtcagcctg     1200
accaattcga aattccagaa caacgagtat ggcgtgattc tcggtcagcc ggacgactcg     1260
gcagccgcca agccgagta  caagggctac ccacggatga caatcgccaa caacgtgttc     1320
agcaacctcg atgtccgcgg gcccggtctg tttcgtcagg ccaatttga  cgtagttaac     1380
aactcgatcg acaaattcca cctcggtttc actgcgaccg ggaacgctac catcctgtcg     1440
caggccaact atttcagcaa cggtgtcgat gtttccaaca aggcaagtaa tagcggcgtg     1500
ctggatgact acggcgatgc gcacttcaaa gacatcggca gtaacgtcag tttcactcag     1560
aaatcgccgg ttaccgcctg gacaccgagc tacaaccggg acgtgaaaac agccgaagca     1620
```

-continued gccagagcct atgacctggc aatgcgggt gcacaggtcg tgaaataa        1668

<210> SEQ ID NO 4
<211> LENGTH: 555
<212> TYPE: PRT
<213> ORGANISM: Pseudomonas syringae

<400> SEQUENCE: 4

Met Asn Thr Ile Asn Arg Asn Ile Tyr Pro Val Gly Ile Ser Ala
  1               5                  10                  15

Gln Asp Ala Pro Val Gln Thr Asp Gln Leu Gln Pro Gln Gly Gln Gly
                 20                  25                  30

Ile Arg Pro Gly His Asn Ser Asn Leu Ile Asp Phe Gly Leu Ile Gln
             35                  40                  45

Gln Ala Asn Gly Pro His Ser Ser Leu Asn Thr Ser Ser Ser Arg Ile
         50                  55                  60

Gln Pro Thr Asp Thr Ser Thr Ser Ser Asn Arg Leu Gly Gly Asn Gly
 65                  70                  75                  80

Asp Gln Leu Leu Asn Lys Leu Val Glu Ala Ile Arg Asn Ile Leu Asn
                 85                  90                  95

Asn Leu Leu Ser Leu Leu Glu Gly Asn Gln His Gln Gly Ser Ser Pro
            100                 105                 110

Ala Gln Thr Gln Arg Glu Gln Thr Pro Thr Ser Thr Gln Ser His Ala
        115                 120                 125

Ser Pro Ser Ser Ser Ser Ser Ser Pro Ser Thr Ser Ser Gln Ser
        130                 135                 140

Ser Pro Ser Val Pro Ser Thr Pro Gln Gly Asn Ala Glu Lys Pro Phe
145                 150                 155                 160

Val Val Gln Ser Asp His Pro Ala Glu Lys Pro Val Ser Leu Gln Arg
                165                 170                 175

Thr Ser Glu Pro Thr Ser Val Thr Pro Pro Gln Thr Pro Pro Gln Ala
            180                 185                 190

Val Glu Arg Asn Ser Ile Thr Pro Asp Lys Ala Pro Ala Lys Pro Glu
        195                 200                 205

Ala Val Lys Pro Ala Val Val Asn Asp Pro Val Leu Pro Lys Thr Ser
    210                 215                 220

Ile Pro Ala Ala Ala Lys Pro Asp Ser Thr Val Thr Ala Ala Lys His
225                 230                 235                 240

Ala Thr Pro Ala Ala Arg Gly Gln Gly Ala Asp Met Ser Gly Met Ile
                245                 250                 255

Gly Phe Ala Lys Glu Ala Asn Thr Thr Gly Gly Asn Asn Gly Glu Val
            260                 265                 270

Val Thr Val Asn Thr Val Ala Asp Leu Lys Lys Tyr Met Glu Asp Asp
        275                 280                 285

Lys Ala Arg Thr Val Lys Leu Gly Ala Asn Leu Ser Ala Asp Ser Lys
    290                 295                 300

Val Ser Ile Asn Phe Gly Ala Asn Lys Thr Leu Leu Gly Thr Asp Lys
305                 310                 315                 320

Gly Asn Thr Leu His Asn Ile Tyr Leu Ala Ser Gly Lys Thr Ala Ser
                325                 330                 335

Asn Asp Ile Phe Gln Asn Leu Asn Phe Asn His Asp Ala Arg Tyr Arg
            340                 345                 350

Glu Asn Gly Asp Met Gln Met Phe Ile Ser Ser Gly Gln Lys Tyr Trp
        355                 360                 365

```
Ile Asp His Ile Thr Ala Thr Gly Thr Lys Asp Gln Asn Pro Lys Gly
    370                 375                 380

Leu Asp Lys Leu Leu Tyr Val Gly Gly Lys Ala Asp Asn Val Ser Leu
385                 390                 395                 400

Thr Asn Ser Lys Phe Gln Asn Asn Glu Tyr Gly Val Ile Leu Gly Gln
                405                 410                 415

Pro Asp Asp Ser Ala Ala Ala Lys Ala Glu Tyr Lys Gly Tyr Pro Arg
            420                 425                 430

Met Thr Ile Ala Asn Asn Val Phe Ser Asn Leu Asp Val Arg Gly Pro
        435                 440                 445

Gly Leu Phe Arg Gln Gly Gln Phe Asp Val Val Asn Asn Ser Ile Asp
    450                 455                 460

Lys Phe His Leu Gly Phe Thr Ala Thr Gly Asn Ala Thr Ile Leu Ser
465                 470                 475                 480

Gln Ala Asn Tyr Phe Ser Asn Gly Val Asp Val Ser Asn Lys Ala Ser
                485                 490                 495

Asn Ser Gly Val Leu Asp Asp Tyr Gly Asp Ala His Phe Lys Asp Ile
            500                 505                 510

Gly Ser Asn Val Ser Phe Thr Gln Lys Ser Pro Val Thr Ala Trp Thr
        515                 520                 525

Pro Ser Tyr Asn Arg Asp Val Lys Thr Ala Glu Ala Ala Arg Ala Tyr
    530                 535                 540

Asp Leu Ala Asn Ala Gly Ala Gln Val Val Lys
545                 550                 555

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
caccatgacc atgggtgttt cac                                          23

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6
agcgggtaaa ttgccctgc                                               19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 7
caccatgaat acgatcaac                                               19

<210> SEQ ID NO 8
<211> LENGTH: 15
<212> TYPE: DNA
<213> ORGANISM: Artificial Sequence
<220> FEATURE:
```

```
<223> OTHER INFORMATION: Description of Artificial Sequence:  Primer

<400> SEQUENCE: 8
tttcacgacc tgtgc                                                        15
```

PSEUDOMONAS SYRINGAE HARPINS, HOPPTOP AND HOPPMAH$_{PTO}$, AND THEIR USES

This application is entitled to priority benefit of U.S. Provisional Patent Application Ser. No. 60/356,408, filed Feb. 12, 2002, and U.S. Provisional Patent Application Ser. No. 60/380,185, filed May 10, 2002, each of which is hereby incorporated by reference in its entirety.

This invention was developed with government funding under National Science Foundation Grant Nos. MCB 9631530, MCB-9982646, and DBI-0077622. The U.S. Government may retain certain rights.

FIELD OF THE INVENTION

The present invention relates to new hypersensitive response elicitor proteins or polypeptides of *Pseudomonas syringae* and their uses.

BACKGROUND OF THE INVENTION

Interactions between bacterial pathogens and their plant hosts generally fall into two categories: (1) compatible (pathogen-host), leading to intercellular bacterial growth, symptom development, and disease development in the host plant; and (2) incompatible (pathogen-nonhost), resulting in the hypersensitive response, a particular type of incompatible interaction occurring, without progressive disease symptoms. During compatible interactions on host plants, bacterial populations increase dramatically and progressive symptoms occur. During incompatible interactions, bacterial populations do not increase, and progressive symptoms do not occur.

The hypersensitive response ("HR") is a rapid, localized necrosis that is associated with the active defense of plants against many pathogens (Horsfall et al., eds., *Plant Disease: An Advanced Treatise* Vol. 5, pp. 201–224, New York, N.Y.: Academic Press (1980); Mount et al., eds., *Phytopathogenic Prokaryotes*, Vol. 2, pp. 149–177, New York, N.Y.: Academic Press (1982)). The hypersensitive response elicited by bacteria is readily observed as a tissue collapse if high concentrations ($\geq 10^7$ cells/ml) of a limited host-range pathogen like *Pseudomonas syringae* or *Erwinia amylovora* are infiltrated into the leaves of nonhost plants (necrosis occurs only in isolated plant cells at lower levels of inoculum) (Klement, *Nature* 199:299–300 (1963); Klement et al., *Phytopathology* 54:474–477 (1963); Turner et al., *Phytopathology* 64:885–890 (1974); Mount et al., eds., *Phytopathogenic Prokaryotes*, Vol. 2., pp. 149–177, New York, N.Y.: Academic Press (1982)). The capacities to elicit the hypersensitive response in a nonhost and be pathogenic in a host appear linked. As noted by Mount et al., eds., *Phytopathogenic Prokaryotes*, Vol. 2., pp. 149–177, New York, N.Y.: Academic Press (1982), these pathogens also cause physiologically similar, albeit delayed, necroses in their interactions with compatible hosts. Furthermore, the ability to produce the hypersensitive response or pathogenesis is dependent on a common set of genes, denoted hrp (Lindgren et al., *J. Bacteriol.* 168:512–22 (1986); Willis et al., *Mol. Plant-Microbe Interact.* 4:132–138 (1991)). Consequently, the hypersensitive response may hold clues to both the nature of plant defense and the basis for bacterial pathogenicity.

The hrp genes are widespread in gram-negative plant pathogens, where they are clustered, conserved, and in some cases interchangeable (Willis et al., *Mol. Plant-Microbe Interact.* 4:132–138 (1991); Dangl, ed., *Current Topics in Microbiology and Immunology: Bacterial Pathogenesis of Plants and Animals-Molecular and Cellular Mechanisms*, pp. 79–98, Berlin: Springer-Verlag (1994)). Several hrp genes encode components of a protein secretion pathway similar to one used by *Yersinia*, *Shigella*, and *Salmonella* spp. to secrete proteins essential in animal diseases (Van Gijsegem et al., *Trends Microbiol.* 1:175–180 (1993)). In *E. amylovora*, *P. syringae*, and *P. solanacearum*, hrp genes have been shown to control the production and secretion protein elicitors of the hypersensitive response (He et al., *Cell* 73:1255–1266 (1993); Wei et al., *J. Bacteriol.* 175: 7958–7967 (1993); Arlat et al., *EMBO J.* 13:543–553 (1994)). Hypersensitive response elicitor proteins, designated harpins, are proteins found in phytopathogens containing a type III secretion system and are typically glycine-rich, acidic, cysteine-lacking, heat stable proteins (He et al., *Cell* 73: 1255–1266 (1993).

The first of these proteins was discovered in *E. amylovora* Ea321, a bacterium that causes fire blight of rosaceous plants, and was designated harpin (Wei et al., *Science* 257:85–88 (1992)). Mutations in the encoding hrpN gene revealed that harpin is required for *E. amylovora* to elicit a hypersensitive response in nonhost tobacco leaves and incite disease symptoms in highly susceptible pear fruit. The *P. solanacearum* GMI1000 PopA1 protein has similar physical properties and also elicits the hypersensitive response in leaves of tobacco, which is not a host of that strain (Arlat et al., *EMBO J.* 13:543–53 (1994)). However, *P. solanacearum* popA mutants still elicit the hypersensitive response in tobacco and incite disease in tomato. Thus, the role of these glycine-rich hypersensitive response elicitors can vary widely among gram-negative plant pathogens.

Other plant pathogenic hypersensitive response elicitors have been isolated, cloned, and sequenced from various organisms, including: HrpW from *Erwinia amylovora* (Kim et al., *J. Bacteriol.* 180(19):5203–5210 (1998)); HrpN from *Erwinia chrysanthemi* (Bauer et al., *MPMI* 8(4): 484–91 (1995)); HrpN from *Erwinia carotovora* (Cui et al., *MPMI* 9(7): 565–73 (1996)); HrpN from *Erwinia stewartii* (Ahmad et al., 8*th Int'l. Cong. Molec. Plant-Microb. Inter.* Jul. 14–19, 1996 and Ahmad et al., *Ann. Mtg. Am. Phytopath. Soc.* Jul. 27–31, 1996); hreX from *Xanthomonas campestris* (U.S. Patent Application Publ. No. 20020066122 to Wei et al.); HrpZ from *Pseudomonas syringae* pv. *syringae* (He et al., *Cell* 73:1255–1266 (1993); WO 94/26782 to Cornell Research Foundation, Inc.); and HrpW from *Pseudomonas syringae* pv. tomato (Charkowski et al., *J. Bacteriol.* 180: 5211–5217 (1998)).

In electron microscopy studies, both HrpW and HrpZ of *Pseudomonas syringae* are associated with the type III secretion system pilus (Jin et al., *Science* 294:2556–2558 (2001); Jin et al., *Molecular Microbiology* 40:1129–1139 (2001)), suggesting that harpins work with the pilus to facilitate protein delivery into the plant cell. A *P. syringae* strain containing chromosomal deletions of hrpZ and hrpW has a reduced ability to cause the HR on nonhost plants, but it retains normal virulence on tomato (Charkowski et al., *J. Bacteriol.* 180:5211–5217 (1998)). This phenotype indicates that it is likely that there are more harpins in the genome.

The present invention is a further advance in the effort to identify, clone, and sequence hypersensitive response elicitor proteins or polypeptides from plant pathogens.

SUMMARY OF THE INVENTION

The present invention is directed to isolated proteins or polypeptides which elicit a hypersensitive response in plants as well as isolated DNA molecules which encode the hypersensitive response eliciting proteins or polypeptides.

The hypersensitive response eliciting proteins or polypeptides can be used to impart disease resistance, stress resistance, and enhanced growth to plants or plants grown from treated seeds, to control insects on plants or plants grown from treated plant seeds, to impart post-harvest disease or desiccation resistance in fruits or vegetables, to impart enhanced longevity of fruit or vegetable ripeness, to impart desiccation resistance to cuttings of ornamental plants, and/or promote early flowering of ornamental plants. This involves applying the hypersensitive response elicitor protein or polypeptide in a non-infectious form to plants, plant seeds, cuttings removed from plants, and/or fruits or vegetables removed from plants under conditions effective to impart disease resistance, stress resistance, and enhanced growth to plants or plants grown from treated seeds, to control insects on plants or plants grown from treated plant seeds, to impart post-harvest disease or desiccation resistance in fruits or vegetables, to impart enhanced longevity of fruit or vegetable ripeness, to impart desiccation resistance to cuttings of ornamental plants, and/or promote early flowering of ornamental plants.

As an alternative to applying the hypersensitive response elicitor protein or polypeptide to plants or plant seeds in order to impart disease resistance, stress resistance, and enhanced growth to plants or plants grown from treated seeds, to control insects on plants or plants grown from treated plant seeds, to impart post-harvest disease or desiccation resistance in fruits or vegetables, to impart enhanced longevity of fruit or vegetable ripeness, to impart desiccation resistance to cuttings of ornamental plants, and/or promote early flowering of ornamental plants, transgenic plants or plant seeds can be utilized. When utilizing transgenic plants, this involves providing a transgenic plant transformed with a DNA molecule encoding a hypersensitive response elicitor protein or polypeptide and growing the plant under conditions effective to impart disease resistance, stress resistance, and enhanced growth to plants, to control insects on plants, to impart post-harvest disease or desiccation resistance in fruits or vegetables, to impart enhanced longevity of fruit or vegetable ripeness, to impart desiccation resistance to cuttings of transgenic ornamental plants, and/or promote early flowering of transgenic ornamental plants. Alternatively, a transgenic plant seed transformed with the DNA molecule encoding a hypersensitive response elicitor protein or polypeptide can be provided and planted in soil. A plant is then propagated under conditions effective to impart disease resistance, stress resistance, and enhanced growth to plants grown from the transgenic seeds, to control insects on plants grown from the transgenic plant seeds, to impart post-harvest disease or desiccation resistance in fruits or vegetables, to impart enhanced longevity of fruit or vegetable ripeness, to impart desiccation resistance to cuttings of the transgenic ornamental plants, and/or promote early flowering of the transgenic ornamental plants.

The present invention is also directed to a composition including a carrier and a protein or polypeptide of the present invention which elicits a hypersensitive response in plants. The composition may also include an additive such as fertilizer, insecticide, fungicide, nematacide, and mixtures of these additives.

DETAILED DESCRIPTION OF THE INVENTION

Figure 1:
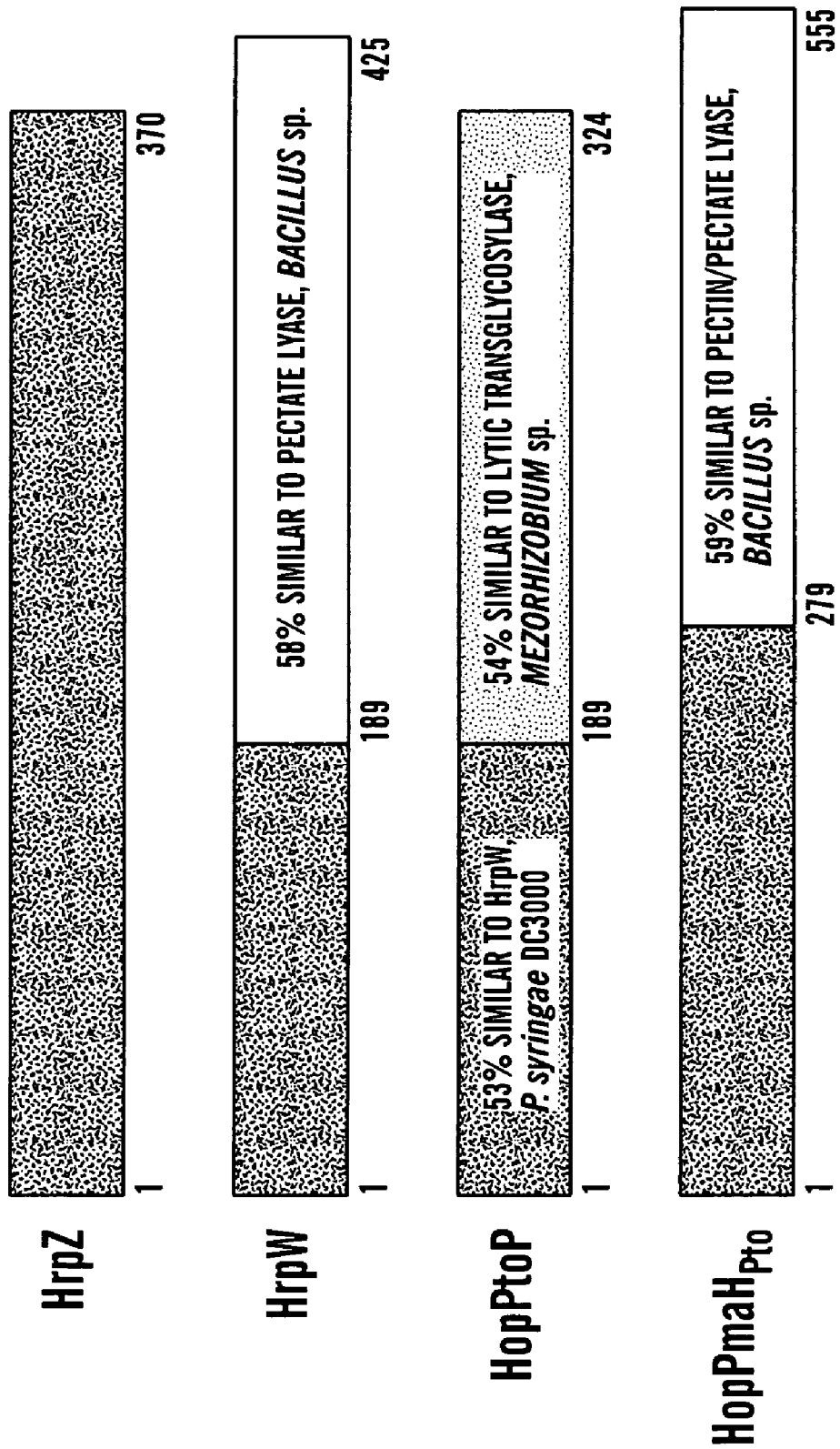
FIG. 1 illustrates a comparison between the amino acid sequences of HrpZ, HrpW, HopPtoP, and HopPmaH from *Pseudomonas syringae*. Harpin proteins were analyzed using BLAST, and the percent similarities shown were determined using protein-protein BLAST. Like HrpZ and HrpW, two previously identified harpins (see He et al., *Cell* 73:1255–1266 (1993); Charkowski et al., *J. Bacteriol.* 180: 5211–5217 (1998), each of which is hereby incorporated by reference in its entirety), HopPtoP and HopPmaH$_{Pto}$ have N-terminal domains with no predicted function. The C-terminal domains of HopPtoP and HopPmaH$_{Pto}$ show homologies to protein domains with enzymatic function. Lytic transglycosylases normally break down peptidoglycan in the bacterial cell wall, while pectin and pectate lyases break down pectin in the plant cell wall.

The present invention relates to an isolated DNA molecule having the nucleotide sequence of SEQ ID NO: 1 as follows:

```
atgaccatgg gtgtttcacc tattcgtaac tcaaactccc tgccgatcga tttttcgtcg   60
ttgagcgcaa agagtggcgg gcataacggg ctgggcagcg gagacaattc gactatcgac  120
```

-continued

```
ccgagtacgt tgttgttcgg caatcaaggg cagacgcagg tcaatttcgc tccgcccaac  180
agcacggact cctcaaccag cggtgtgaac gctgcgtcag gcaatacggc gtccggcctg  240
gtcgagcaaa tcatgagcct gctgaaacaa ttgatgcaga tgctgatgca aaacaacaat  300
gcttccggta accctcagac tgattcgtca acgccaggcg tcggcagtgg caacagcgtc  360
gggagcggcg gtactggaag cagtctcgca ggcagtgacg gtggcgacga aacgtccggt  420
gtcggtaacg gcggtttagg cgacgcgggc agcacgccaa caacgagcgc ggccgatggt  480
gtgccctcgg atacttcact cacgggtagc ggtgggctgc atttgcctca acagcttgag  540
cagtatcgag gcgacattat ggacgccgcc aaagccaccg gcgtgccggc cagcgtgatc  600
gccgggcaga tatgggctga gtcgcgcggt cagttgaatg cggccaccac caatgtcaac  660
ggcaaggcca tgcgggcct gatgcaggtc aacgcagaca cgttcaagtc attgcagcag  720
caaaacccgg ggttgctggg caacgacgtc aacgattcgc acaccaacat catggcgggc  780
gcgctctacc tgcgagacca gaacaaggag ttcggcgaca tggggcagc acttcgcgca  840
tacaactccg ggcccgacaa ggtcaataaa gccgacctca gcgacacggg aggcgtgggc  900
ggcagcagct acccggcgga cgtactgaac ttcgcgaaaa tcatcgagag tgggcagggc  960
aatttacccg cttga  975
```

This DNA molecule of the present invention encodes a protein or polypeptide having the amino acid sequence of SEQ ID NO: 2 as follows:

```
Met Thr Met Gly Val Ser Pro Ile Arg Asn Ser Asn
  1               5                      10
Ser Leu Pro Ile Asp Phe Ser Ser Leu Ser Ala Lys
           15                  20
Ser Gly Gly His Asn Gly Leu Gly Ser Gly Asp Asn
 25               30                  35
Ser Thr Ile Asp Pro Ser Thr Leu Leu Phe Gly Asn
              40                  45
Gln Gly Gln Thr Gln Val Asn Phe Ala Pro Pro Asn
    50                  55                  60
Ser Thr Asp Ser Ser Thr Ser Gly Val Asn Ala Ala
              65                  70
Ser Gly Asn Thr Ala Ser Gly Leu Val Glu Gln Ile
           75                  80
Met Ser Leu Leu Lys Gln Leu Met Gln Met Leu Met
 85               90                  95
Gln Asn Asn Asn Ala Ser Gly Asn Pro Gln Thr Asp
             100                 105
Ser Ser Thr Pro Gly Val Gly Ser Gly Asn Ser Val
           110                 115                 120
Gly Ser Gly Gly Thr Gly Ser Ser Leu Ala Gly Ser
                 125                 130
Asp Gly Gly Asp Gln Thr Ser Gly Val Gly Asn Gly
         135                 140
Gly Leu Gly Asp Ala Gly Ser Thr Pro Thr Thr Ser
 145                 150                 155
Ala Ala Asp Gly Val Pro Ser Asp Thr Ser Leu Thr
             160                 165
Gly Ser Gly Gly Leu His Leu Pro Gln Gln Leu Glu
         170                 175                 180
Gln Tyr Arg Gly Asp Ile Met Asp Ala Ala Lys Ala
                 185                 190
Thr Gly Val Pro Pro Ser Val Ile Ala Gly Gln Ile
             195                 200
Trp Ala Glu Ser Arg Gly Gln Leu Asn Ala Ala Thr
 205                 210                 215
Thr Asn Val Asn Gly Lys Ala Asp Ala Gly Leu Met
             220                 225
Gln Val Asn Ala Asp Thr Phe Lys Ser Leu Gln Gln
         230                 235                 240
Gln Asn Pro Gly Leu Leu Gly Asn Asp Val Asn Asp
             245                 250
Ser His Thr Asn Ile Met Ala Gly Ala Leu Tyr Leu
         255                 260
Arg Asp Gln Asn Lys Glu Phe Gly Asp Met Gly Ala
 265                 270                 275
Ala Leu Arg Ala Tyr Asn Ser Gly Pro Asp Lys Val
                 280                 285
Asn Lys Ala Asp Leu Ser Asp Thr Gly Gly Val Gly
     290                 295                 300
Gly Ser Ser Tyr Pro Ala Asp Val Leu Asn Phe Ala
                 305                 310
Lys Ile Ile Glu Ser Gly Gln Gly Asn Leu Pro Ala
             315                 320
```

This protein or polypeptide (also referred to herein as "HopPtoP") has a predicted molecular mass of about 32 kDa and an isoelectric point of about 4.13. Like other hypersensitive response elicitors, the above protein is glycine rich (~15%), lacks cysteine, is sensitive to proteases, is temperature stable, is secreted via a type III secretion system (where it appears to be targeted to the plant apoplast), and is capable of inducing a hypersensitive response following infiltration onto plant tissues of non-host plants. Like HrpW, HopPtoP has a striking 2-domain structure with the N-terminal portion being "harpin-like" (aa 1–189) and the second portion having homology to lytic transglycosylate (aa 190–324). The harpin domain of HopPtoP possess approximately 53% similarity and 34% identity to the corresponding harpin domain of HrpW from *Pseudomonas syringae* from DC3000. The lytic transglycosylate domain of HopPtoP shares about 54% similarity to a lytic transglycosylase of *Mezorhizobium* sp. Based on these similarities, HopPtoP is considered a homolog of HrpW.

The present invention also relates to an isolated DNA molecule having the nucleotide sequence of SEQ ID NO: 3 as follows:

```
atgaatacga tcaacagaaa catctacccc gtctccggga tttctgcgca ggatgccct   60
gtacaaactg atcagctcca gccgcaaggc cagggcatca ggccggggca caatagcaac  120
ctgatcgact tcggactgat acagcaggcc aatggtccgc actcatcgct gaacacatcg  180
agctccagaa ttcagccgac tgacaccagc acatcctcaa acaggctggg gggtaatggc  240
gatcagttac tgaacaaact cgtggaagcg atccgtaata tcctcaacaa cctgctctct  300
ctgctggaag gcaatcaaca ccagggctct tcgcctgcac agacccagcg tgaacagacg  360
ccgacgtcca ctcaatcgca cgcttcgcct tcctcgtcgt cttcatcttc gccgtcgaca  420
tcctcccagt cttcaccctc agtgccttca acgcctcagg gcaacgcaga aaaaccgttt  480
gtggtgcaga gcgatcatcc ggcggaaaaa ccggtatcgc tgcagagaac ctcagagcca  540
acgtctgtga cgccgccaca aacaccaccg caggctgtcg agcgaaacag cattaccccg  600
gacaaggcac cggccaaacc cgaagcggta aagccggcag tggtcaacga cccggtgctg  660
ccgaaaacct cgatccctgc cgccgccaag cctgacagca cggtgaccgc cgcaaaacac  720
gcgacgcccg ctgcccgtgg ccagggcgct gacatgtccg gcatgatcgg ttttgccaag  780
gaagccaata ccaccggggg caacaacggc gaagtggtca ccgtgaacac ggttgccgac  840
ctcaagaagt acatggagga cgacaaagcc cgcaccgtca agctgggggc caacctgtct  900
gccgacagta aagtgtcgat aaatttcggg gccaacaaaa ccctgctggg caccgataaa  960
ggcaacaccc tgcacaacat ctatctggcc agcggcaaga ccgccagcaa cgacattttc 1020
cagaatctga acttcaacca cgacgcccgt taccgtgaaa acggcgacat gcagatgttc 1080
atcagcagcg gtcagaaata ctggatcgac cacatcaccg ctaccggaac caaggatcag 1140
aacccccaaag gtctggataa actgctctac gtgggcggca aggcagataa cgtcagcctg 1200
accaattcga aattccagaa caacgagtat ggcgtgattc tcggtcagcc ggacgactcg 1260
gcagccgcca aagccgagta caagggctac ccacggatga caatcgccaa caacgtgttc 1320
agcaacctcg atgtccgcgg gcccggtctg tttcgtcagg gccaatttga cgtagttaac 1380
aactcgatcg acaaattcca cctcggtttc actgcgaccg ggaacgctac catcctgtcg 1440
caggccaact atttcagcaa cggtgtcgat gtttccaaca aggcaagtaa tagcggcgtg 1500
ctggatgact acggcgatgc gcacttcaaa gacatcggca gtaacgtcag tttcactcag 1560
aaatcgccgg ttaccgcctg gacaccgagc tacaaccggg acgtgaaaac agccgaagca 1620
gccagagcct atgacctggc caatgcgggt gcacaggtcg tgaaataa              1668
```

This DNA molecule of the present invention encodes a protein or polypeptide having the amino acid sequence of SEQ ID NO: 4 as follows:

```
Met Asn Thr Ile Asn Arg Asn Ile Tyr Pro Val Ser
 1               5                      10
Gly Ile Ser Ala Gln Asp Ala Pro Val Gln Thr Asp
             15                  20
Gln Leu Gln Pro Gln Gly Gln Gly Ile Arg Pro Gly
 25              30                      35
His Asn Ser Asn Leu Ile Asp Phe Gly Leu Ile Gln
                 40                  45
Gln Ala Asn Gly Pro His Ser Ser Leu Asn Thr Ser
 50                  55                      60
Ser Ser Arg Ile Gln Pro Thr Asp Thr Ser Thr Ser
 65                      70
Ser Asn Arg Leu Gly Gly Asn Gly Asp Gln Leu Leu
             75                  80
Asn Lys Leu Val Glu Ala Ile Arg Asn Ile Leu Asn
 85                  90                      95
Asn Leu Leu Ser Leu Leu Glu Gly Asn Gln His Gln
                 100                 105
Gly Ser Ser Pro Ala Gln Thr Gln Arg Glu Gln Thr
     110                 115                 120
Pro Thr Ser Thr Gln Ser His Ala Ser Pro Ser Ser
                 125                 130
Ser Ser Ser Ser Ser Pro Ser Thr Ser Ser Gln Ser
     135                 140
Ser Pro Ser Val Pro Ser Thr Pro Gln Gly Asn Ala
145             150                 155
Glu Lys Pro Phe Val Val Gln Ser Asp His Pro Ala
                 160                 165
Glu Lys Pro Val Ser Leu Gln Arg Thr Ser Glu Pro
     170                 175                 180
Thr Ser Val Thr Pro Pro Gln Thr Pro Pro Gln Ala
                 185                 190
Val Glu Arg Asn Ser Ile Thr Pro Asp Lys Ala Pro
     195                 200
Ala Lys Pro Glu Ala Val Lys Pro Ala Val Val Asn
205                 210                 215
Asp Pro Val Leu Pro Lys Thr Ser Ile Pro Ala Ala
                 220                 225
Ala Lys Pro Asp Ser Thr Val Thr Ala Ala Lys His
     230                 235                 240
Ala Thr Pro Ala Ala Arg Gly Gln Gly Ala Asp Met
                 245                 250
Ser Gly Met Ile Gly Phe Ala Lys Glu Ala Asn Thr
             255                 260
Thr Gly Gly Asn Asn Gly Glu Val Val Thr Val Asn
265                 270                 275
Thr Val Ala Asp Leu Lys Lys Tyr Met Glu Asp Asp
                 280                 285
Lys Ala Arg Thr Val Lys Leu Gly Ala Asn Leu Ser
     290                 295                 300
Ala Asp Ser Lys Val Ser Ile Asn Phe Gly Ala Asn
                 305                 310
Lys Thr Leu Leu Gly Thr Asp Lys Gly Asn Thr Leu
                 315                 320
His Asn Ile Tyr Leu Ala Ser Gly Lys Thr Ala Ser
325                 330                 335
Asn Asp Ile Phe Gln Asn Leu Asn Phe Asn His Asp
                 340                 345
Ala Arg Tyr Arg Glu Asn Gly Asp Met Gln Met Phe
Ile Ser Ser Gly Gln Lys Tyr Trp Ile Asp His Ile
                 350                 355                 360
Thr Ala Thr Gly Thr Lys Asp Gln Asn Pro Lys Gly
                 365                 370
Leu Asp Lys Leu Leu Tyr Val Gly Gly Lys Ala Asp
                 375                 380
Asn Val Ser Leu Thr Asn Ser Lys Phe Gln Asn Asn
385                 390                 395
Glu Tyr Gly Val Ile Leu Gly Gln Pro Asp Asp Ser
                 400                 405
Ala Ala Ala Lys Ala Glu Tyr Lys Gly Tyr Pro Arg
     410                 415                 420
Met Thr Ile Ala Asn Asn Val Phe Ser Asn Leu Asp
                 425                 430
Val Arg Gly Pro Gly Leu Phe Arg Gln Gly Gln Phe
                 435                 440
Asp Val Val Asn Asn Ser Ile Asp Lys Phe His Leu
445                 450                 455
Gly Phe Thr Ala Thr Gly Asn Ala Thr Ile Leu Ser
                 460                 465
Gln Ala Asn Tyr Phe Ser Asn Gly Val Asp Val Ser
     470                 475                 480
Asn Lys Ala Ser Asn Ser Gly Val Leu Asp Asp Tyr
                 485                 490
Gly Asp Ala His Phe Lys Asp Ile Gly Ser Asn Val
                 495                 500
Ser Phe Thr Gln Lys Ser Pro Val Thr Ala Trp Thr
505                 510                 515
Pro Ser Tyr Asn Arg Asp Val Lys Thr Ala Glu Ala
                 520                 525
Ala Arg Ala Tyr Asp Leu Ala Asn Ala Gly Ala Gln
     530                 535                 540
Val Val Lys
         545                 550
```

This protein or polypeptide (also referred to herein as "HopPmaH$_{Pto}$") has a predicted molecular mass of about 59 kDa and an isoelectric point of about 7.65. Like other hypersensitive response elicitors, the above protein is glycine rich (~7.5%), lacks cysteine, is sensitive to proteases, is temperature stable, is secreted via a type III secretion system, and is capable of inducing a hypersensitive response following infiltration onto plant tissues of non-host plants. Like HrpW, HopPmaH$_{Pto}$ has a striking 2-domain structure with the N-terminal portion (aa 1–279) being "harpin-like" and the second portion (aa 280–555) having homology to pectin/pectate lyase. The pectate-lyase domain is about 60% similar and about 43% identical to the pectate/pectin lyase from *Bacillus subtilis* (Accession No. AF027868, which is hereby incorporated by reference in its entirety). Within the lyase domain, HopPmaH$_{Pto}$ is overall about 30% similar and 22% identical to the pectate/pectin lyase from *B. subtilis*.

Fragments of the above hypersensitive response elicitor polypeptides or proteins are encompassed by the present invention. Suitable fragments can include those portions of the harpin proteins that contain the harpin-like domain.

Suitable fragments can be produced by several means. In the first approach, subclones of the gene encoding the elicitor protein of the present invention are produced by conventional molecular genetic manipulation by subcloning gene fragments. The subclones then are expressed in vitro or in vivo in bacterial cells to yield a smaller protein or peptide that can be tested for elicitor activity according to the procedure described below, e.g., in Wei et al., *Science* 257:85–86 (1992), which is hereby incorporated by reference in its entirety.

As an alternative approach, fragments of an elicitor protein can be produced by digestion of a full-length elicitor protein with proteolytic enzymes like chymotrypsin or *Staphylococcus* proteinase A, or trypsin. Different proteolytic enzymes are likely to cleave elicitor proteins at different sites based on the amino acid sequence of the elicitor protein. Some of the fragments that result from proteolysis may be active elicitors of the hypersensitive response.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Also suitable as isolated nucleic acid molecules according to the present invention is a nucleic acid which has a nucleotide sequence that is at least about 55% similar, preferably at least about 65% similar or more preferably at least about 75% similar, to the nucleotide sequence of SEQ ID NO: 1 or SEQ ID NO: 3 by basic BLAST using default parameters analysis. Even more preferred is that such a nucleotide sequence have a nucleic acid identity to the nucleotide sequence of SEQ ID NO: 1 or SEQ ID NO: 3, either by basic BLAST or ClustalW using default parameters analysis, that is at least about 40%, more preferably at least about 50%, and even more preferably at least about 60%. Higher percentages of identity and/or similarity are even more preferred, such as at least about 80% identity and/or at least about 85% similarity.

Also suitable as an isolated nucleic acid according to the present invention is an isolated nucleic acid molecule that hybridizes to the nucleotide sequence of SEQ ID NO: 1 (or its complement) or SEQ ID NO: 3 (or its complement) under suitably stringent hybridization conditions. Exemplary stringent conditions include the use of a hybridization medium or buffer that contains 5×SSC buffer at a temperature of about 42°–65° C., with hybridization being carried out for about 18–20 hours. Stringency can, of course, be increased by lowering the salt concentration or increasing the temperature at which hybridization occurs. Thus, in another embodiment, the hybridization temperature is between about 52°–60° C. In yet another embodiment, the hybridization is between 55°–57° C. Another example of suitable high stringency conditions is when hybridization is carried out at 65° C. for 20 hours in a medium containing 1M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, 50 μm g/ml *E. coli* DNA. Wash conditions can be selected at varying stringency requirements, as long as the wash conditions are suitable to remove non-specifically bound nucleic acid molecules. Typically, when nucleic acid molecules of longer than about 200 bases are used as probes in hybridization protocols (such as radiolabeled DNA molecules of SEQ ID NO: 1 or SEQ ID NO: 3), the importance of the wash conditions is minimized. See Sambrook et al., *Molecular Cloning: A Laboratory Manual*, Second Edition, Cold Spring Harbor Press, NY (1989), which is hereby incorporated by reference in its entirety. Thus, a series of increasingly stringent wash conditions can be performed, beginning with lower stringency conditions and continuing until the stringency conditions of the hybridization procedure is achieved. The series of washes can be performed for suitable time periods, typically anywhere from about 15 minutes up to about 2 hours, although shorter or longer washes are certainly effective. However, any DNA molecules hybridizing to the DNA molecule of SEQ ID NO: 1 (or its complement) or SEQ ID NO: 3 (or its complement) under such stringent conditions must not be identical to the nucleic acids encoding the HrpW hypersensitive response elicitor proteins or polypeptides of *Erwinia amylovora* (see Kim et al., *J. Bacteriol.* 180(19): 5203–5210 (1998), which is hereby incorporated by reference in its entirety) or *Pseudomonas syringae* pv. tomato (see Charkowski et al., *J. Bacteriol.* 180:5211–5217 (1998), which is hereby incorporated by reference in its entirety).

The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Such secretion can be performed in accordance with the protocol established in PCT Application Publ. No. WO 00/02996 to Bauer et al., which is hereby incorporated by reference in its entirety. Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, differential pressure, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by high performance liquid chromatography ("HPLC").

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e., not normally present). The heterologous DNA molecule is inserted into the expression system or vector in proper sense orientation and correct reading frame. The vector contains the necessary elements for the transcription and translation of the inserted protein-coding sequences. As discussed more fully below, the elements for transcription and translation differ depending on the type of system being employed (e.g., eukaryotic vs. prokaryotic, and plant vs. animal).

The present invention also relates to an expression vector containing a DNA molecule encoding a hypersensitive response elicitor protein. The nucleic acid molecule of the present invention may be inserted into any of the many available expression vectors using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation.

A variety of vectors are available for stable transformation using *Agrobacterium tumefaciens*, a soilborne bacterium that causes crown gall. Crown gall is characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant chromosomal DNA. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens*. See Fraley et al., *Proc. Nat'l Acad. Sci.*, 80:4803–4807 (1983), which is hereby incorporated by reference in its entirety.

Other suitable vectors for practicing the present invention include, but are not limited to, the following viral vectors such as lambda vector system gt11, gtWES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from LaJolla, Calif., which is hereby incorporated by reference in its entirety), pQE, pIH821, pGEX, pET series (Studier et al., *Methods in Enzymology.* 185:60–89 (1990) which is hereby incorporated by reference in its entirety), and any derivatives thereof. Any appropriate vectors now known or later described for genetic transformation are suitable for use with the present invention. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccinia virus. Recombinant viruses can be generated by transfection of plasmids into cells infected with virus.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

In one aspect of the present invention, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include, without limitation, the nopoline synthase (NOS) gene promoter from *Agrobacterium tumefaciens* (U.S. Pat. No. 5,034,322 to Rogers et al., which is hereby incorporated by reference in its entirety), the cauliflower mosaic virus (CaMv) $^{35}$S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), the ubiquitin promoter, which is a gene product known to accumulate in many cell types, the enhanced 35S promoter described in U.S. Pat. No. 5,106,739 to Comai et al. (which is hereby incorporated by reference in its entirety), the dual $^{35}$S promoter, the FMV promoter from figwort mosaic virus that is described in U.S. Pat. No. 5,378,619 to Rogers et al. (which is hereby incorporated by reference in its entirety), the RI T-DNA promoter described in U.S. Pat. No. 5,466,792 to Slightom et al. (which is hereby incorporated by reference in its entirety), the octopine T-DNA promoter described in U.S. Pat. No. 5,428,147 to Barker et al. (which is hereby incorporated by reference in its entirety), the alcohol dehydrogenase 1 promoter (Callis et al., *Genes Dev.*, 1(10):1183–1200 (1987), which is hereby incorporated by reference in its entirety), the patatin promoter B33 (Rocha-Sosa et al., *EMBO J.*, 8:23–29 (1989), which is hereby incorporated by reference in its entirety), the E8 promoter (Deikman et al., *EMBO J.*, 7(11):3315–3320 (1988), which is hereby incorporated by reference in its entirety), the beta-conglycin promoter (Tierney et al., *Planta*, 172:356–363 (1987), which is hereby incorporated by reference in its entirety), the acid chitinase promoter (Samac et al., *Plant Physiol.*, 93:907–914 (1990), which is hereby incorporated by reference in its entirety), the Arabidopsis histone H4 promoter described in U.S. Pat. No. 5,491,288 to Chaubet et al. (which is hereby incorporated by reference in its entirety), or the recombinant promoter for expression of genes in monocots described in U.S. Pat. No. 5,290,924 to Last et al. (which is hereby incorporated by reference in its entirety).

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 to Shewmaker et al., which is hereby incorporated by reference in its entirety).

In one aspect of the present invention, the inducible promoter is a pathogen-inducible promoter. Such promoters include those from pathogenesis-related proteins (e.g., PR proteins, SAR proteins, beta-1,3-glucanase, chitinase), which are induced following infection by a pathogen (see, e.g., Redolfi et al., *Neth. J. Plant Pathol.* 89:245–254 (1983); Uknes et al., *Plant Cell* 4:645–656 (1992); and Van Loon, *Plant Mol. Virol.* 4:111–116 (1985), which are hereby incorporated by reference in their entirety). Another aspect of the present invention involves promoters that are expressed locally at or near the site of pathogen infection (see, e.g., Marineau et al., *Plant Mol. Biol.* 9:335–342 (1987); Matton et al., *Molecular Plant-Microbe Interactions* 2:325–331 (1989); Somsisch et al., *Proc. Natl. Acad. Sci. U.S.A.* 83:2427–2430 (1986); Somsisch et al., *Molecular and General Genetics* 2:93–98 (1988); and Yang, *Proc. Natl. Acad. Sci. U.S.A.* 93:14972–14977 (1996), which are hereby incorporated by reference in their entirety). See also Chen et al., *Plant J.* 10:955–966 (1996); Zhang and Sing, *Proc. Natl. Acad. Sci. U.S.A.* 91:2507–2511 (1994); Warner et al., *Plant J.* 3:191–201 (1993); Siebertz et al., *Plant Cell* 1:961–968 (1989), which are hereby incorporated by reference in their entirety).

Additionally, as pathogens find entry into plants through wounds or insect damage, a wound inducible promoter may be used in the construct of the invention. Such wound inducible promoters include potato proteinase inhibitor (pin II) gene (Ryan, *Ann. Rev. Phytopath.* 28:425–449 (1990); Duan et al., *Nature Biotechnology* 14:494–498 (1996), which are hereby incorporated by reference in its entirety); wun1 and wun2, U.S. Pat. No. 5,428,148 to Reddy et al. (which is hereby incorporated by reference in its entirety); win1 and win2 (Stanford et al., *Mol. Gen. Genet.* 215: 200–208 (1989), which is hereby incorporated by reference in its entirety); systemin (McGurl et al., *Science* 255: 1570–1573 (1992), which is hereby incorporated by reference in its entirety); WIP1 (Rohrmeier et al., *Plant Mol Biol* 22:783–792 (1993); Eckelkamp et al., *FEBS Letters* 323: 73–76 (1993), which are hereby incorporated by reference in their entirety); and MPI gene (Cordero et al., *Plant Journal* 6(2): 141–150 (1994), which is hereby incorporated by reference in its entirety).

The DNA construct of the present invention also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase 3' regulatory region (Fraley et al., *Proc. Nat'l Acad. Sci. USA* 80:4803–4807 (1983), which is hereby incorporated by reference in its entirety) and the cauliflower mosaic virus 3' regulatory region (Odell et al., *Nature* 313(6005):810–812 (1985), which is hereby incorporated by reference in its entirety). Virtually any 3' regulatory region known to be operable in plants would suffice for proper expression of the coding sequence of the DNA construct of the present invention.

The vector of choice, promoter, and an appropriate 3' regulatory region can be ligated together to produce the DNA construct of the present invention using well known molecular cloning techniques as described in Sambrook et al., *Molecular Cloning: A Laboratory Manual*, Second Edition, Cold Spring Harbor Press, NY (1989), and Ausubel et al., *Current Protocols in Molecular Biology*, John Wiley & Sons, New York, N.Y. (1989), which are hereby incorporated by reference in their entirety.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention further relates to methods of imparting disease resistance, stress resistance, and enhanced growth to plants or plants grown from treated seeds, controlling insects on plants or plants grown from treated plant seeds, imparting post-harvest disease or desiccation resistance in fruits or vegetables, imparting enhanced longevity of fruit or vegetable ripeness, imparting desiccation resistance to cuttings of ornamental plants, and/or promoting early flowering of ornamental plants. These methods involve applying a hypersensitive response elicitor polypeptide or protein in a non-infectious form to all or part of a plant, plant seed, cutting, and/or fruit or vegetable under conditions where the polypeptide or protein contacts all or part of the cells of the plant, plant seed, cutting, and/or fruit or vegetable. Alternatively, the hypersensitive response elicitor protein or polypeptide can be applied to plants such that seeds recovered from such plants themselves are able to impart disease resistance, stress resistance, and enhanced growth to plants grown from those seeds, to control insects on plants grown from those seeds, to impart post-harvest disease or desiccation resistance in fruits or vegetables harvested from plants grown from those seeds, to impart enhanced longevity of fruit or vegetable ripeness for fruits or vegetables harvested from plants grown from those seeds, to impart desiccation resistance to cuttings of ornamental plants grown from those seeds, and/or promote early flowering of ornamental plants grown from those seeds.

Application of the hypersensitive response elicitor polypeptide or protein in non-infectious form can be carried out in a number of ways including, without limitation: 1) application of an isolated elicitor polypeptide or protein; 2) application of bacteria which do not cause disease and are transformed with genes encoding a hypersensitive response elicitor polypeptide or protein; and 3) application of bacteria which cause disease in some plant species (but not in those to which they are applied) and naturally contain a gene encoding the hypersensitive response elicitor polypeptide or protein.

In one embodiment of the present invention, the hypersensitive response elicitor polypeptide or protein of the present invention can be isolated directly from *Pseudomonas syringae* pv. tomato as described in the Examples infra. Preferably, however, the isolated hypersensitive response elicitor polypeptide or protein of the present invention is produced recombinantly and purified as described supra.

In other embodiments of the present invention, the hypersensitive response elicitor polypeptide or protein of the present invention can be applied to plants or plant seeds by applying bacteria containing genes encoding the hypersensitive response elicitor polypeptide or protein. Such bacteria must be capable of secreting or exporting the polypeptide or protein so that the elicitor can contact plant or plant seed cells. In these embodiments, the hypersensitive response elicitor polypeptide or protein is produced by the bacteria in planta or on seeds or just prior to introduction of the bacteria to the plants or plant seeds.

In one embodiment of the bacterial application mode of the present invention, the bacteria do not cause the disease and have been transformed (e.g., recombinantly) with genes encoding a hypersensitive response elicitor polypeptide or protein. For example, *E. coli*, which does not elicit a hypersensitive response in plants, can be transformed with genes encoding a hypersensitive response elicitor polypeptide or protein and optionally type III secretion systems (U.S. patent application Ser. No. 09/350,852 to Bauer et al., filed Jul. 9, 1999, which is hereby incorporated by reference in its entirety), and then applied to plants. Bacterial species other than *E. coli* can also be used in this embodiment of the present invention.

In another embodiment of the bacterial application mode of the present invention, the bacteria do cause disease and naturally contain a gene encoding a hypersensitive response elicitor polypeptide or protein. Examples of such bacteria are noted above. However, in this embodiment, these bacteria are applied to plants or their seeds which are not susceptible to the disease carried by the bacteria. For example, *Pseudomonas syringae* pv. tomato causes disease in tomato but not in beans. However, such bacteria will elicit a hypersensitive response in beans. Accordingly, in accordance with this embodiment of the present invention, *Pseudomonas syringae* pv. tomato can be applied to bean plants or seeds to impart disease resistance to plants, enhance plant growth, and control insects on plants or plants grown from the plant seeds, impart stress resistance to plants, and/or impart post-harvest disease or desiccation resistance in fruits or vegetables, without causing disease in that species.

The method of the present invention can be utilized to treat a wide variety of plants, their seeds, their cuttings, and/or their harvested fruit or vegetables to impart disease resistance, stress resistance, and enhanced growth to plants or plants grown from treated seeds, to control insects on plants or plants grown from treated plant seeds, to impart post-harvest disease or desiccation resistance in fruits or vegetables, to impart enhanced longevity of fruit or vegetable ripeness, to impart desiccation resistance to cuttings of ornamental plants, and/or promote early flowering of ornamental plants.

Suitable plants include dicots and monocots. More particularly, useful crop plants can include, without limitation: alfalfa, rice, wheat, barley, rye, cotton, sunflower, peanut, corn, potato, sweet potato, bean, pea, chicory, lettuce, endive, cabbage, brussel sprouts, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. As used herein, ornamental plants are those plants that are not crop plants. Examples of suitable ornamental plants include, without limitation: *Arabidopsis thaliana, Saintpaulia*, petunia, pelargonium, poinsettia, chrysanthemum, carnation, rose, tulip, and zinnia.

With regard to the use of the hypersensitive response elicitor protein or polypeptide of the present invention in imparting disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi (see WO 96/39802 to Wei et al. and WO 98/24297 to Qiu et al., which are hereby incorporated by reference in their entirety). Resistance, inter alia, to the following viruses can be achieved by the method of the present invention: Tobacco mosaic virus and Tomato mosaic virus. Resistance, inter alia, to the following bacteria can also be imparted to plants in accordance with present invention: *Pseudomonas solancearum, Pseudomonas syringae* pv. *tabaci*, and *Xanthamonas campestris* pv. *pelargonii*. Plants can be made resistant, inter alia, to the following fungi by use of the method of the present invention: *Fusarium oxysporum* and *Phytophthora infestans.*

With regard to the use of the hypersensitive response elicitor protein or polypeptide of the present invention to enhance plant growth, various forms of plant growth enhancement or promotion can be achieved (WO 98/32844 to Qiu et al., which is hereby incorporated by reference in its entirety). This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

Another aspect of the present invention is directed to effecting any form of insect control for plants (WO 98/37752 to Zitter et al., which is hereby incorporated by reference in its entirety). For example, insect control according to the present invention encompasses preventing insects from contacting plants to which the hypersensitive response elicitor has been applied, preventing direct insect damage to plants by feeding injury, causing insects to depart from such plants, killing insects proximate to such plants, interfering with insect larval feeding on such plants, preventing insects from colonizing host plants, preventing colonizing insects from releasing phytotoxins, etc. The present invention also prevents subsequent disease damage to plants resulting from insect infection.

The present invention is effective against a wide variety of insects. European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, and tomato pinworm. Collectively, this group of insect pests represents the most economically important group of pests for vegetable production worldwide.

The present invention relates to the use of the hypersensitive response elicitors of the present invention to impart stress resistance to plants (WO 00/28055 to Wei et al., which is hereby incorporated by reference in its entirety). Resistance can be afforded to a variety of stresses, such as any environmental factor having an adverse effect on plant physiology and development. Examples of such environmental stress include without limitation: climate-related stress (e.g., drought, water, frost, cold temperature, high temperature, excessive light, and insufficient light), air pollution stress (e.g., carbon dioxide, carbon monoxide, sulfur dioxide, $NO_X$, hydrocarbons, ozone, ultraviolet radiation, acidic rain), chemical (e.g., insecticides, fungicides, herbicides, heavy metals), and nutritional stress (e.g., fertilizer, micronutrients, macronutrients).

The present invention is also effective in imparting post-harvest disease or desiccation resistance in fruits or vegetables (WO 01/80639 to Wei et al., which is hereby incorporated by reference in its entirety), as well as imparting desiccation resistance to cuttings of ornamental plants (WO 02/37960 to Wei et al., which is hereby incorporated by reference in its entirety). The present invention also relates to ornamental cuttings that have themselves been treated with a hypersensitive response elicitor protein or polypeptide of the present invention following removal from an ornamental plant, as well as cuttings removed from ornamental plants that have been treated therewith. The present invention also includes fruit or vegetable products that have been treated with a hypersensitive response elicitor protein or polypeptide of the present invention or removed from plants that have been treated therewith.

In addition to imparting post-harvest disease or desiccation resistance, the longevity of fruit or vegetable ripeness can be enhanced (WO 01/80639 to Wei et al., which is hereby incorporated by reference in its entirety). Enhanced ripeness longevity will afford a longer shelf-life to produce and thereby promote less consumer waste.

The method of the present invention involving application of the hypersensitive response elicitor polypeptide or protein can be carried out through a variety of procedures when all or part of the plant is treated, including leaves, stems, roots, propagules (e.g., cuttings), etc. This may (but need not) involve infiltration of the hypersensitive response elicitor polypeptide or protein into the plant. Suitable application methods include high or low pressure spraying, injection, and leaf abrasion proximate to when elicitor application takes place. Seed treatments can also be employed, as described in U.S. Pat. No. 6,235,974 to Qiu et al., which is hereby incorporated by reference in its entirety. When treating plant seeds, in accordance with the application embodiment of the present invention, the hypersensitive response elicitor protein or polypeptide can be applied by low or high pressure spraying, coating, immersion, or injection (U.S. Pat. No. 6,235,974 to Qiu et al., which is hereby incorporated by reference in its entirety). Other suitable application procedures can be envisioned by those skilled in the art provided they are able to effect contact of the hypersensitive response elicitor polypeptide or protein with cells of the plant or plant seed. Once treated with the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the hypersensitive response elicitor protein or polypeptide to impart disease resistance, stress resistance, and enhanced growth to plants or plants grown from treated seeds, to control insects on plants or plants grown from treated plant seeds, to impart post-harvest disease or desiccation resistance in fruits or vegetables, to impart enhanced longevity of fruit or vegetable ripeness, to impart desiccation resistance to cuttings of ornamental plants, and/or promote early flowering of ornamental plants.

The hypersensitive response elicitor polypeptide or protein can be applied to plants or plant seeds in accordance with the present invention alone or in a mixture with other materials. Alternatively, the hypersensitive response elicitor polypeptide or protein can be applied separately to plants with other materials being applied at different times.

A composition suitable for treating plants or plant seeds in accordance with the application embodiment of the present invention contains a hypersensitive response elicitor polypeptide or protein in a carrier. Suitable carriers include water, aqueous solutions, slurries, or dry powders. By way of example, one such composition of harpin$_{Ea}$ (3 wt %) is commercially available from Eden Bioscience Corp. under the tradename Messenger®. It is expected that compositions of the proteins of the present invention can be prepared in a manner similar to that which is used for Messenger®.

Although not required, the composition of the present invention may contain additional additives including fertilizer, insecticide, fungicide, nematacide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response elicitor polypeptide or protein can be applied to plant seeds with other conventional seed formulation and treatment materials, including clays and polysaccharides.

As an alternative to applying a hypersensitive response elicitor polypeptide or protein to plants or plant seeds in order to impart disease resistance, stress resistance, and enhanced growth to plants or plants grown from treated seeds, to control insects on plants or plants grown from treated plant seeds, to impart post-harvest disease or desiccation resistance in fruits or vegetables, to impart enhanced longevity of fruit or vegetable ripeness, to impart desiccation resistance to cuttings of ornamental plants, and/or promote early flowering of ornamental plants, transgenic plants or plant seeds can be utilized (WO 01/95724 to Wei et al., which is hereby incorporated by reference in its entirety). Using transgenic plants involves providing a transgenic plant transformed with a DNA molecule encoding a hypersensitive response elicitor polypeptide or protein of the present invention and growing the plant under conditions effective to permit that DNA molecule to impart disease resistance, stress resistance, and enhanced growth to the transgenic plants, to control insects on the transgenic plants, to impart post-harvest disease or desiccation resistance in fruits or vegetables removed from the transgenic plants, to impart enhanced longevity of fruit or vegetable ripeness, to impart desiccation resistance to cuttings of transgenic ornamental plants, and/or promote early flowering of transgenic ornamental plants. Alternatively, a transgenic plant seed transformed with a DNA molecule encoding a hypersensitive response elicitor polypeptide or protein of the present invention can be provided and planted in soil. A plant is then propagated from the planted seed under conditions effective to permit that DNA molecule to impart disease resistance, stress resistance, and enhanced growth to plants grown from the transgenic seeds, to control insects on plants grown from the transgenic plant seeds, to impart post-harvest disease or desiccation resistance in fruits or vegetables removed from the transgenic plants, to impart enhanced longevity of fruit or vegetable ripeness, to impart desiccation resistance to cuttings of transgenic ornamental plants, and/or promote early flowering of transgenic ornamental plants.

In the alternative embodiment of the present invention involving the use of transgenic plants and transgenic seeds, a hypersensitive response elicitor polypeptide or protein need not but may be applied topically to the transgenic plants or transgenic plant seeds.

The vector described above can be microinjected directly into plant cells by use of micropipettes to transfer mechanically the recombinant DNA. Crossway, *Mol. Gen. Genetics,* 202:179–85 (1985), which is hereby incorporated by reference in its entirety. The genetic material may also be transferred into the plant cell using polyethylene glycol. Krens et al., *Nature,* 296:72–74 (1982), which is hereby incorporated by reference in its entirety.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies. Fraley et al., *Proc. Natl. Acad. Sci. USA,* 79:1859–63 (1982), which is hereby incorporated by reference in its entirety.

The DNA molecule may also be introduced into the plant cells by electroporation. Fromm et al., *Proc. Natl. Acad. Sci. USA,* 82:5824 (1985), which is hereby incorporated by reference in its entirety. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome (Schell, *Science,* 237:1176–83 (1987), which is hereby incorporated by reference in its entirety).

After transformation, the transformed plant cells can be selected (using appropriate selection media to identify transformants) and then regenerated. Plant regeneration from cultured protoplasts is described in Evans et al., *Handbook of Plant Cell Cultures, Vol.* 1: MacMillan Publishing Co., New York (1983); and Vasil I. R. (ed.), *Cell Culture and Somatic Cell Genetics of Plants,* Acad. Press, Orlando, Vol. I (1984) and Vol. III (1986), which are hereby incorporated by reference in their entirety. It is known that practically all plants can be regenerated from cultured cells or tissues.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedures. Transgenic seeds can, of course, be recovered from the transgenic plants. These seeds can then be planted in the soil and cultivated using conventional procedures to produce transgenic plants.

When transgenic plants and plant seeds are used in accordance with the present invention, they additionally can be treated with the same materials as are used topically to treat the plants and seeds. These other materials, including hypersensitive response elicitors, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the hypersensitive response elicitor to impart disease resistance, stress resistance, and enhanced growth to plants, to control insects on plants, to impart post-harvest disease or desiccation resistance in fruits or vegetables, to impart enhanced longevity of fruit or vegetable ripeness, to impart desiccation resistance to cuttings of ornamental plants, and/or promote early flowering of ornamental plants.

Such plants may also be treated with conventional plant treatment agents (e.g., insecticides, fertilizers, etc.). The present invention also relates to fruit or vegetables removed from transgenic plants of the present invention as well as cuttings removed from transgenic ornamental plants of the present invention.

In the embodiment of the present invention where transgenic plants or plant seeds are utilized, it should be appreciated that the transgenic plants or plant seeds can include one or more transgenes other than the transgene encoding the hypersensitive response elicitor protein or polypeptide of the present invention. In particular, the use of hypersensitive response elicitors for the purpose of maximizing the benefit of a transgenic trait or overcoming a concomitant yield penalty is disclosed in U.S. patent application Ser. No. 09/880,371 to Wei et al., filed Jun. 13, 2001 (now published), which is hereby incorporated by reference in its entirety.

EXAMPLES

Each of the Examples set forth below is intended to illustrate the nature of the present invention but is by no means intended to limit its scope.

Example 1

Isolation of HopPtoP and HopPmaH$_{Pto}$ DNA Molecules and Preparation of Expression Vectors hopPtoP was identified by using a reporter transposon to identify genes in the P. s. tomato DC3000 genome that were induced in a HrpL-dependent manner (Fouts et al., *Proc. Natl. Acad. Sci. USA* 99(4):2275–2280 (2002) and supplemental materials available online, which are hereby incorporated by reference in their entirety). hopPmaH$_{Pto}$ was identified by the bioinformatic approach of scanning the DC3000 genome with a Hidden Markov Model for Hrp promoter sequences (Fouts et al., *Proc. Natl. Acad. Sci. USA* 99(4):2275–2280 (2002) and supplemental materials available online, which are hereby incorporated by reference in their entirety). The HrpL-dependent expression of hopPmaH$_{Pto}$ was then confirmed by microarray analysis.

The following primers were used to amplify hopPtoP and hopPmaH$_{Pto}$ from *P. syringae* pv. tomato DC3000 genomic DNA using standard PCR protocols:

```
hopPtoP forward primer
caccatgacc atgggtgttt cac    23   (SEQ ID NO:5)

hopPtoP reverse primer
agcgggtaaa ttgccctgc          19   (SEQ ID NO:6)

hopPmaH_Pto forward primer
caccatgaat acgatcaac          19   (SEQ ID NO:7)

hopPmaH_Pto reverse primer
tttcacgacc tgtgc              15   (SEQ ID NO:8)
```

Blunt end PCR fragments were generated for use with Invitrogen™ Gateway™ technology in accordance with the manufacturer's instructions. PCR products were cloned into pENTR/SD/D-TOPO® vector using Gateway™ technology. The Gateway™ technology offers a universal cloning process based on the site-specific recombination properties of bacteriophage lambda, and provides a rapid and highly efficient way to move DNA sequences into multiple vector systems for functional analysis and protein expression.

Briefly, the attachment sites for the vector can recombine with each other. Thus, once an entry clone is created with the pENTR cloning kit, the fragment/gene of interest can easily be cloned into numerous other vectors that contain complementary attachment sites with which the pENTR attachment sites can recombine.

pENTR/SD/D-TOPO®:: hopPtoP and pENTR/SD/D-TOPO®:: hopPmaH$_{Pto}$ were used to clone into pET-DEST42, a 'Gateway-ized' vector from Invitrogen™. This placed 6×-histidine and V5 epitope tags to the C-terminal ends of hopPtoP and hopPmaH$_{Pto}$. The resulting plasmids were designated pCPP5098 (hopPtoP-6×His-V5) and pCPP5099 (hopPmaH$_{Pto}$-6×His-V5). These plasmids were transformed into *E. coli* BL21 DE3 from Novagen. QIAGEN protein purification protocols were used to optimize purification under native conditions. For HopPtoP, conditions described in Alfano et al. (*Molecular Microbiology* 19:715–728 (1996), which is hereby incorporated by reference in its entirety) were used for purification and expression. The conditions described in Alfano et al., *Molecular Microbiology* 19:715–728 (1996), which is hereby incorporated by reference in its entirety, can also be used for purification and expression of HopPmaH$_{Pto}$. In addition, standard conditions well known in the art for growing *E. coli* (Sambrook et al., *Molecular Cloning: A Laboratory Manual*, Second Edition, Cold Spring Harbor Press, NY (1989), which is hereby incorporated by reference in its entirety), as well as for purifying His-tagged proteins (Hainfeld et al., *Microsc. Microanal.* 8(Supp. 2):832CD (2002); Hochuli et al., *J. Chromatogr.* 411:177–184 (1987); Hainfeld et al., *J. Struct. Biol.* 127:185–198 (1999); Buchel et al., *J. Mol. Biol.* 312:371–379 (2001); Hata et al., *J. Virol. Methods* 84(2):117–126 (2000); Blanc et al., *J. Virol. Methods* 77(1):11–15 (1999); and Schmidbauer et al., *Biochemica* 3:22–24 (1997), which are hereby incorporated by reference in their entirety), can be used to purify and express HopPtoP and HopPmaH$_{Pto}$.

Example 2

Figure 2:
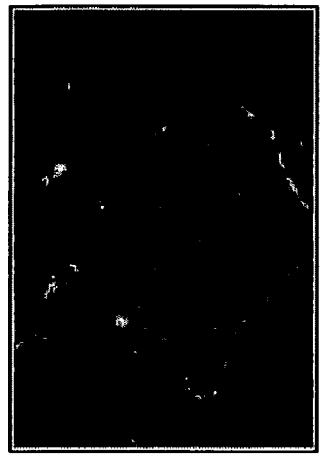
FIG. 2 shows the results of protein infiltration onto leaf surfaces and the resulting elicitation of a hypersensitive response ("HR"). HrpZ, HopPtoP, and HopPmaH$_{Pto}$ were purified using a 6×His tag system, and denatured at 100° C. for 10 minutes. Proteins were infiltrated into *Nicotiana tabacum* cv. Xanthi, and the hypersensitive response was photographed at 24 hours.
Figure 2:
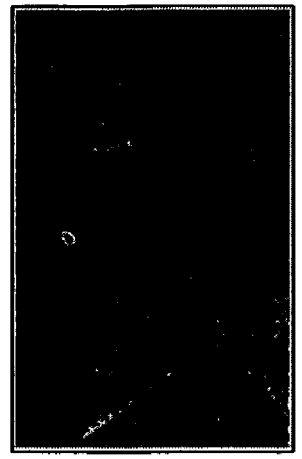
Figure 2:
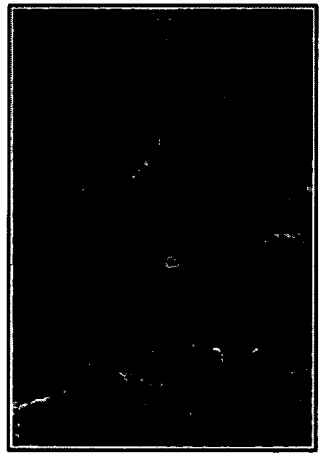
Figure 2:
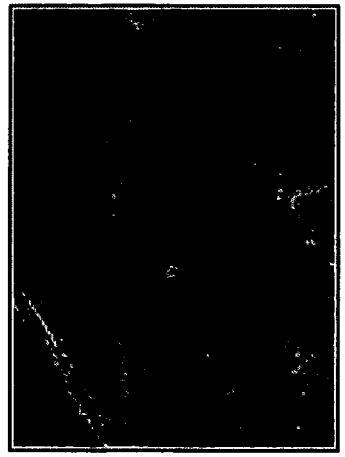

Topical Application of the HopPtoP and HopPmaH$_{Pto}$ to Plants and HR Activity Thereof Purified protein preparations prepared in accordance with Example 1 above were used to infiltrate HopPtoP or HopPmaH$_{Pto}$ onto plant tissues. Purified HrpZ was similarly prepared. HrpZ, HopPtoP, and HopPmaH$_{Pto}$ were purified using a 6×His tag system, and denatured at 100° C. for 10 minutes. Proteins were then infiltrated into *Nicotiana tabacum* cv. xanthi, and the hypersensitive response was photographed at 24 hours (Alfano et al., *Mol. Microbiol.* 19:715–728 (1996), which is hereby incorporated by reference in its entirety). As shown in FIG. 2, like HrpZ, which is known to elicit a hypersensitive response in tobacco plant tissues, HopPtoP and HopPmaH$_{Pto}$ elicit a similar hypersensitive response, while no such response could be detected from the negative control.

Example 3

HopPtoP and HopPmaH$_{Pto}$ Proteins are Secreted in Culture pENTR/SD/D-TOPO®:: hopPtoP and pENTR/SD/D-TOPO®:: hopPmaH$_{Pto}$ were used to clone into pCPP3234, an IPTG-inducible "Gateway-ized" vector created in the lab by cloning Gateway Reading Frame B fragment into SmaI site of pCPP3214. pCPP3214 has a cyaA construct for gene fusions in broad host range vector pVLT35 (de Lorenzo et al., *Gene* 123:17–24 (1993), which is hereby incorporated by reference in its entirety) and was constructed by digesting pMJH$_{20}$ with SacI and HindIII, and ligating this fragment to pVLT35 cut with the same enzymes. This fused the adenylate cyclase (cyaA) gene to the C-terminal ends of hopPtoP and hopPmaH$_{Pto}$, which provided an eptiope for detection of protein in the cell and supernatant fractions during the secretion assays. The resulting plasmids, pCPP3256 (HopPtoP-CyaA) and pCPP3255 (HopPmaH$_{Pto}$-CyaA), were then transformed into *P. syringae* DC3000 and CUCPB5114 (*P. syringae* DC3000 without the hrp/hrc cluster, negative control).

Bacteria were inoculated in 30 mL Hrp minimal media (induces Hrp system) to OD$_{600}$=0.15 with IPTG to 100 μM. Bacteria were grown under standard conditions and then harvested at OD$_{600}$=0.3. Cultures were centrifuged at 28000 rpm in Beckman L8-70 ultracentrifuge. The top 30 ml supernatant was removed, 7.5 ml trichloroacetic acid (TCA) (~25% TCA solution) was added to precipitate proteins, and the mixture was incubated at 4° C. overnight (>12 hours). Thereafter, supernatant fractions were centrifuged at 28000 rpm in Beckman L8-70 ultracentrifuge to obtain supernatant protein pellet, which was then washed twice with 5 ml 100% acetone. Protein was resuspended in 1×protein loading buffer, 100 μl for every $OD_{600}$=0.3, and used 20 μl for SDS-PAGE analysis. Also, cell pellets (from above) were resuspended in 1 ml dd$H_2O$ for every $OD_{600}$=0.3, and 15 μl was used for SDS-PAGE analysis. Standard SDS-PAGE analysis was used.

Figure 3B:
FIGS. 3A–B illustrate the results of a secretion assay on HopPtoP and HopPmaH$_{Pto}$, respectively. HopPtoP and HopPmaH$_{Pto}$ were tagged at the C-terminus with the adenylate cyclase (CyaA) protein for detection in subsequent Western analysis of the cell pellet (cell) and supernatant (SN). The plasmids were expressed in either *P. syringae* DC3000 or *P. syringae* DC3000 containing a non-functional type III secretion system (Δhrp/hrc). Both proteins are secreted by *P. syringae* DC3000 but not *P. syringae* DC3000 (Δhrp/hrc).
Figure 3B:
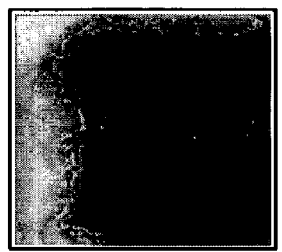
Figure 3A:
Figure 3A:

CyaA antibodies (Santa Cruz Biotech; see Lee et al., Infect. Immun. 67(5):2090–2095 (1999), which is hereby incorporated by reference in its entirety) were used to detect HopPtoP and HopPmaH$_{Pto}$ proteins in the cell and supernatant fractions. As shown in FIG. 3A, HopPtoP-CyaA fusion was detected in subsequent Western analysis of the cell pellet (cell) and supernatant (SN) for P. syringae DC3000, which is known to possess a type III secretion system, but only in the cell pellet for P. syringae DC3000 (Δhrp/hrc), which is lacking a type III secretion system. In FIG. 3B, HopPmaH$_{Pto}$-CyaA fusion was detected in subsequent Western analysis of the cell pellet (cell) and supernatant (SN) for P. syringae DC3000 but only in the cell pellet for P. syringae DC3000 (Δhrp/hrc). Thus, both HopPtoP and HopPmaH$_{Pto}$ fusions were secreted by the type III secretion system of P. syringae of DC3000.

Example 4

HopPtoP and HopPmaH$_{Pto}$ are Translocated into Plant Tissues

Vectors pCPP3256 (HopPtoP-CyaA) and pCPP3255 (HopPmaH$_{Pto}$-CyaA) in P. syringae DC3000, described above, and CUCPB5114 were used for translocation assays. CyaA is the adenylate cyclase domain from the cyclolysin toxin from Bordetella pertussis. This domain uses calmodulin, found only in eukaryotic cells, to produce cAMP from ATP. Therefore, only a CyaA fusion protein that is translocated can produce high levels of cAMP.

Translocation assays were performed by inoculating bacteria in 5 mM MES, pH=5.5 to $OD_{600}$=0.3, to which IPTG was added to 100 μM. The bacteria were infiltrated into tomato cd. Moneymaker. 8 hours post-infiltration, one plant disc was taken from the tomato plant and then crushed with liquid nitrogen. To the crushed plant tissue, 300 μl 0.2M HCl was added and the suspension was frozen at −20° C. The frozen samples were analyzed for cAMP levels with Correlate-EIA Direct cyclic AMP kit from Assay Designs (see Petnicki-Ocwieja et al., Proc. Natl. Acad. Sci. USA 99: 8336–8341 (2002) and accompanying supporting materials available online, which is hereby incorporated by reference in its entirety).

Figure 4:
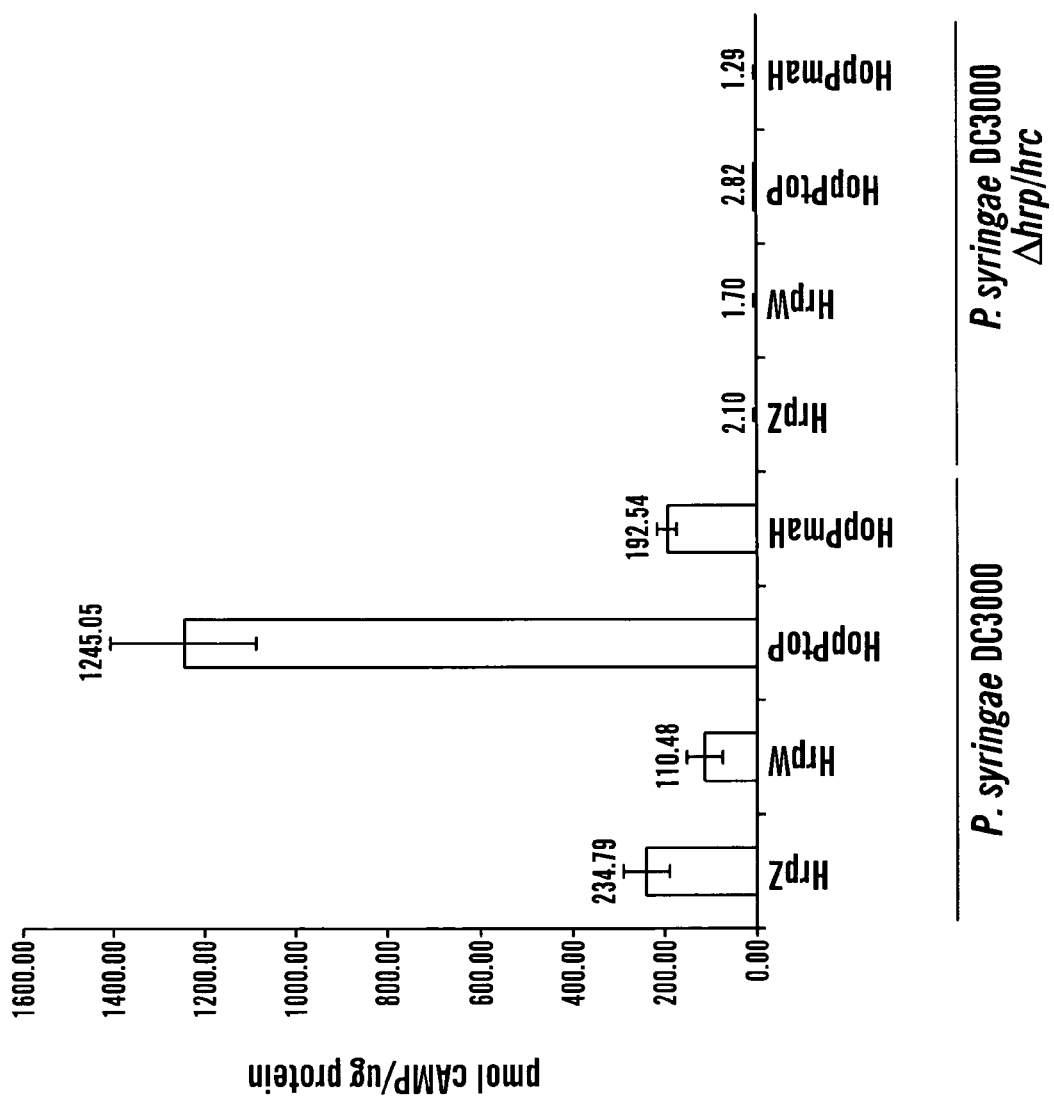
FIG. 4 is a graph depicting the results of a translocation assay on HopPtoP and HopPmaH$_{Pto}$ relative to HrpW and HrpZ. Each harpin gene was fused with the adenylate cyclase (CyaA) reporter gene on an inducible plasmid, and expressed in either *P. syringae* DC3000 or *P. syringae* DC3000 containing a non-functional type III secretion system (Δhrp/hrc). CyaA is activated by the protein calmodulin, which is found only in eukaryotic cells, and produces cAMP from ATP. Increased cAMP levels can be measured, thereby detecting levels of translocation. The strains containing the CyaA fusions were infiltrated into tomato cv. Moneymaker plants, and leaf discs were collected 8 hours post-infiltration for analysis of cAMP levels. Both HopPtoP and HopPmaH$_{Pto}$ are translocated into leaf tissues in the presence of a type III secretion system.

As shown in FIG. 4, HopPtoP and HopPmaH$_{Pto}$, like the known harpins HrpW and HrpZ, were translocated into tomato leaf tissue, as evidenced by the increased cAMP production by P. syringae DC3000 but not P. syringae DC3000 (Δhrp/hrc). In particular, HopPtoP is translocated at significantly higher levels than either HrpW or HrpZ.

Example 5

Transgenic Expression of HopPtoP and HopPmaH$_{Pto}$ in Plants

A variety of technologies have been developed for production of transgenic plants expressing HopPtoP and HopPmaH$_{Pto}$. Each of these technologies relies on the introduction of one of the recombinant hopPtoP and hopPmaH$_{Pto}$ genes of the present invention into a plant cell or tissue and then regenerating the plant cell or tissue into a transgenic plant. The recombinant hopPtoP and hopPmaH$_{Pto}$ genes can contain either an inducible promoter or a constitutive promoter. Since the introduced gene is limited to a single function, other agronomically important traits of the crop plants remain unmodified. Using this technology, transgenic plants transformed with a recombinant hopPtoP or hopPmaH$_{Pto}$ gene can be propagated and grown under conditions effective to impart disease resistance, enhance plant growth, control insects, and impart stress resistance. Transgenic fruit- or vegetable-bearing plants can be useful for imparting post-harvest disease or desiccation resistance in fruits or vegetables, while transgenic ornamental plants can be useful for imparting desiccation resistance to cuttings of ornamental plants and/or promoting early flowering of ornamental plants.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA molecule that encodes a hypersensitive response eliciting protein or polypeptide comprising the amino acid sequence of SEQ ID NO:2.

2. The isolated DNA molecule according to claim 1, wherein said DNA molecule comprises the nucleotide sequence of SEQ ID NO: 1.

3. An expression vector comprising the DNA molecule of claim 1.

4. The expression vector according to claim 3, wherein the DNA molecule is in sense orientation relative to a promoter.

5. A host cell transformed with the DNA molecule of claim 1.

6. The host cell according to claim 5, wherein the host cell is selected from the group consisting of a plant cell and a bacterial cell.

7. The host cell according to claim 4, wherein the DNA molecule is present in an expression vector.

8. A transgenic plant transformed with the DNA molecule of claim 1.

9. The transgenic plant according to claim 8, wherein the plant is selected from the group consisting of alfalfa, rice, wheat, barley, rye, cotton, sunflower, peanut, corn, potato, sweet potato, bean, pea, chicory, lettuce, endive, cabbage, brussel sprouts, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

10. The transgenic plant according to claim 8, wherein the plant is selected from the group consisting of *Arabidopsis thaliana*, *Saintpaulia*, petunia, pelargonium, poinsettia, chrysanthemum, carnation, rose, tulip, and zinnia.

11. A transgenic plant seed transformed with the DNA molecule of claim 1.

12. The transgenic plant seed according to claim 11, wherein the plant seed is selected from the group consisting of alfalfa, rice, wheat, barley, rye, cotton, sunflower, peanut, corn, potato, sweet potato, bean, pea, chicory, lettuce, endive, cabbage, brussel sprouts, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane seeds.

13. The transgenic plant seed according to claim 11, wherein the plant seed is selected from the group consisting of *Arabidopsis thaliana*, *Saintpaulia*, petunia, pelargonium, poinsettia, chrysanthemum, carnation, rose, tulip, and zinnia seeds.

14. A method of imparting disease resistance to plants comprising:
providing a transgenic plant or plant seed transformed with a DNA molecule according to claim 1 and
growing the transgenic plant or transgenic plant produced from the transgenic plant seed under conditions effective to impart disease resistance.

15. The method according to claim 14, wherein a transgenic plant is provided.

16. The method according to claim 14, wherein a transgenic plant seed is provided.

17. A method of enhancing plant growth comprising:
providing a transgenic plant or plant seed transformed with a DNA molecule according to claim 1 and
growing the transgenic plant or transgenic plant produced from the transgenic plant seed under conditions effective to enhance plant growth.

18. The method according to claim 17, wherein a transgenic plant is provided.

19. The method according to claim 17, wherein a transgenic plant seed is provided.

20. A method of insect control for plants comprising:
providing a transgenic plant or plant seed transformed with a DNA molecule according to claim 1 and
growing the transgenic plant or transgenic plant produced from the transgenic plant seed under conditions effective to control insects.

21. The method according to claim 20, wherein a transgenic plant is provided.

22. The method according to claim 20, wherein a transgenic plant seed is provided.

23. A method of imparting post-harvest disease resistance or desiccation resistance to a fruit or vegetable comprising:
providing a transgenic fruit or vegetable plant or plant seed transformed with a DNA molecule according to claim 1 and
growing the transgenic plant or transgenic plant produced from the transgenic plant seed under conditions effective to impart post-harvest disease resistance or desiccation resistance to fruits or vegetables removed from the transgenic plant.

24. The method according to claim 23, wherein a transgenic plant is provided.

25. The method according to claim 23, wherein a transgenic plant seed is provided.

26. A method of enhancing the longevity of fruit or vegetable ripeness comprising:
providing a transgenic fruit or vegetable plant or plant seed transformed with a DNA molecule according to claim 1 and
growing the transgenic plant or transgenic plant produced from the transgenic plant seed under conditions effective to enhance the longevity of ripeness for fruits or vegetables harvested therefrom.

27. The method according to claim 26, wherein a transgenic plant is provided.

28. The method according to claim 26, wherein a transgenic plant seed is provided.

29. A method of imparting desiccation resistance to ornamental plant cuttings comprising:
providing a transgenic ornamental plant or plant seed transformed with a DNA molecule according to claim 1 and growing the transgenic plant or transgenic plant produced from the transgenic plant seed under conditions effective to impart desiccation resistance to a cutting from the transgenic plant.

30. The method according to claim 29, wherein a transgenic plant is provided.

31. The method according to claim 29, wherein a transgenic plant seed is provided.

32. A method of promoting early flowering of ornamental plants comprising:

providing a transgenic ornamental plant or plant seed transformed with a DNA molecule according to claim 1 and growing the transgenic plant or transgenic plant produced from the transgenic plant seed under conditions effective to promote early flowering in the transgenic plant.

33. The method according to claim 32, wherein a transgenic plant is provided.

34. The method according to claim 32, wherein a transgenic plant seed is provided.

35. A method of imparting stress resistance to plants comprising:

providing a transgenic plant or plant seed transformed with a DNA molecule according to claim 1 and growing the transgenic plant or transgenic plant produced from the transgenic plant seed under conditions effective to impart stress resistance to the transgenic plant.

36. The method according to claim 35, wherein a transgenic plant is provided.

37. The method according to claim 35, wherein a transgenic plant seed is provided.

38. A method of imparting desiccation resistance to cuttings removed from ornamental plants comprising:

providing a transgenic ornamental plant or plant seed transformed with a DNA molecule according to claim 1 and growing the transgenic plant or transgenic plant produced from the transgenic plant seed under conditions effective to impart desiccation resistance to cuttings removed from the ornamental plant.

39. The method according to claim 38, wherein a transgenic plant is provided.

40. The method according to claim 38, wherein a transgenic plant seed is provided.

* * * * *